United States Patent
Marx et al.

(10) Patent No.: US 6,777,028 B1
(45) Date of Patent: Aug. 17, 2004

(54) WORK PIECE AND METHOD FOR PRODUCING AND UTILIZING SAID WORK PIECE

(76) Inventors: Rudolf Marx, Ahrtalstrasse 31, 53533 Eichenbach (DE); Horst Fischer, Melatener Weg 20, 52074 Aachen (DE)

( * ) Notice: Subject to any disclaimer, the term of this patent is extended or adjusted under 35 U.S.C. 154(b) by 0 days.

(21) Appl. No.: 10/049,435

(22) PCT Filed: Aug. 10, 2000

(86) PCT No.: PCT/DE00/02702
§ 371 (c)(1),
(2), (4) Date: Jun. 14, 2002

(87) PCT Pub. No.: WO01/12131
PCT Pub. Date: Feb. 22, 2001

(30) Foreign Application Priority Data

Aug. 13, 1999 (DE) .......................... 199 37 864

(51) Int. Cl.$^7$ ............................. B05B 5/10; B05B 3/00; B05B 1/38; B32B 27/30; B32B 27/38
(52) U.S. Cl. .................... 427/207.1; 427/294; 427/295; 427/296; 427/402; 427/535; 427/569; 428/335; 428/353; 428/354; 428/413; 428/414; 428/420; 428/447; 428/448; 428/450; 428/523

(58) Field of Search ................................. 428/446, 447, 428/448, 450, 451, 343, 353, 332, 334, 335, 354, 413, 414, 420; 427/294, 295, 296, 297, 255.18, 2.1, 2.24, 2.26, 2.27, 535, 532, 569, 402, 207.1; 156/305, 307.1, 310

(56) References Cited

U.S. PATENT DOCUMENTS 5,270,350 A 12/1993 Muller et al.
5,770,301 A * 6/1998 Murai et al. ................ 428/213

* cited by examiner

Primary Examiner—Philip Tucker
Assistant Examiner—Michael J Feely
(74) Attorney, Agent, or Firm—David C. Purdue; John C. Purdue

(57) ABSTRACT

A cleaned, sterile ceramic, metallic or polymeric substrate surface is vapor-deposited under sterile conditions with silica, is wetted on top of this with a saline coupling agent under sterile conditions, and is provided on top of the latter with a preserving protective layer which is sterile and/or can be sterilized after polymerization and constitutes the activatable first component of a multi-component adhesive which at the time of use is formed by addition of at least one further adhesive component. A workpiece which has been partially or completely coated in this way can be connected with good adhesion to a polymer, even after several months of sterile storage and transportation, by means of the activation of the protective layer with a monomer.

10 Claims, No Drawings

WORK PIECE AND METHOD FOR PRODUCING AND UTILIZING SAID WORK PIECE

This application is a 371 of PCT/DE00/02702 filed Aug. 10, 2000.

The invention relates to a workpiece with a substrate of ceramic, metal or polymer, the substrate having a surface which is conditioned to form a stable connection with a polymer and which is provided with a silica layer and, on top of this, with a silane coupling agent. The invention also relates to methods for producing and for making use of the workpiece according to the invention.

For the production of dental crowns, it is known from U.S. Pat. No. 4,364,731 to sputter a silica layer onto a cleaned ceramic, metallic or polymeric substrate surface, to apply a silane coupling agent thereon, and finally to apply a polymeric end layer ("plastic veneering"). Such a coating procedure has to be completed in one location and within a very short space of time since otherwise, if the silane coupling layer is left exposed, physical or chemical damage to the extremely sensitive surface can occur, for example as a result of abrasion, a macroscopic impurity, for example in the form of skin flakes, or chemical contamination of the reactive layer surface, for example by reaction with nitrogen, hydrocarbons or other air constituents. According to this method, it is not possible to store and transport the workpieces coated with silica alone and those provided with silane coupling agent, and with the polymeric end coating only taking place later and/or at another location.

In the case of a dental crown which has been veneered in this way, routine dental work does not demand any sterility in the sense of freedom from germs. It is usually simply cleaned with ethanol. The requirement for sterility of a dental crown would also not be consistent with practice, since a dental crown, after production by the dental technician, is packed without special requirements in respect of sterility. On arrival at the dentist's surgery and before it is fitted, it is handled by the dentist and by his assistant, albeit with observation of certain hygiene procedures, but also be contact with the fingers. The nature of its handling thus rules out the continuation of any sterility that might be present. When fitted in the mouth, the crown is immediately colonized by numerous germs and other microorganisms typically found in the mouth, so that any previous sterility would be pointless. Even the healthy oral cavity is in fact "physiologically" heavily colonized by germs at all times. This flora is important for digestion since the digestive process is initiated by the saliva in the mouth.

Also, in the case of such a dental crown, a polymeric coating does not in any way act as a protective layer against physical, mechanical or other stresses. It is instead an aesthetic veneer (typical thickness 1 mm) for in most cases a metal crown, and sometimes also for a ceramic or polymeric dental crown. Veneering with plastic is not intended to provide a protective function for the base of the crown. For example, there is no protection against:

a) physical abrasion: mastication function (the base of the crown itself is substantially more resistant to abrasion than the polymeric veneer) or b) chemical influences: corrosive attack by saliva, food and medications, microbial effects, e.g. by acid excretion of bacteria (the base of the crown, in particular when noble metals or ceramics are used, is substantially more stable to corrosion than is the plastic coating), or c) the influence of temperature changes when eating: these changes can, as a result of different coefficients of expansion, induce cyclically alternating stresses which impair the mechanical stability (the base of the crown is much more resistant to these cycles than is the veneer).

It should be noted that in general (in Germany) the base of the crown is made of an alloy with a high gold content. Ni and CoCr alloys are also commonly used (also known as superalloys from weapons technology), and also Pd-based alloys (only biocompatible to a limited extent; these economy alloys are controversial since they have a high allergy potential) or unalloyed titanium (except for the colour and the difficult processing, they are equal to gold alloys in terms of the above aspects). All the alloys are configured for oral stability and this is guaranteed in particular in the case of alloys having a high gold content. The plastic veneering as a measure for improving aesthetics does not provide additional oral stability; nor is this the intention. On account of their material properties, plastics are in fact less stable in principle in the mouth than are highly corrosion-resistant metals or ceramics.

The plastic veneers are primarily used for the temporary and removable tooth replacement (possibility of repair, given the high abrasion and cracking of the plastic).

The dental crown produced with the layer system of "substrate, silica layer, silane layer, plastic veneer" thus represents a finished product which can be used in this form in the patient.

The object of the present invention now is to make available a workpiece in the form of a semi-finished product, in particular a semi-finished implant or semi-finished prosthesis, with a good capacity for bonding to at least one component of a multi-component adhesive to be applied thereon, the semi-finished product being intended to have a surface which can remain sterile until the later application of the adhesive component and which is suitable for storage and also for transportation.

Methods for producing and for making use of the workpiece according to the invention are also provided.

According to the invention, in the case of a workpiece of the type mentioned in the introduction, the object is achieved by the fact that the substrate, the silica layer and the silane coupling agent are sterile, and that, on top of the silane coupling agent, there is a preserving protective layer which is sterile and/or can be sterilized after polymerization and which constitutes the activatable first component of a multi-component adhesive which at the time of use is formed by addition of at least one further adhesive component.

For the layered structure between substrate and protective layer and multi-component adhesive, freedom from germs is absolutely imperative, unlike the case of the dental crown, since, once the layer system of the semi-finished product is finished, any germs which may possibly be present in the layer system can no longer be removed. Only with a layer system that has been prepared in this way is it possible to guarantee friction-free use, e.g. as hip prosthesis or knee prosthesis. If the layer structure is not germ-free, there is a risk of infections in the body, which must absolutely be avoided. Such infections are difficult to combat especially as the patient's resistance is weakened as a result of the intensive surgical procedure. The infection may possibly result in the first hip endoprosthesis having to be removed in an extensive surgical procedure, measures being taken to combat the infection, and a second hip endoprosthesis being implanted. It must be noted at this point that such a hip operation can only be carried out a maximum of three to four times on any one patient.

By means of the preserving protective layer, the silane coupling agent is chemically sealed off and consequently can no longer be physically or chemically contaminated. The layer thickness of the protective layer is additionally sufficient to withstand a small amount of friction. A workpiece is thus made available which can be stored and transported. Larger numbers of semi-finished products can thus be produced at one production site and later provided with the additional adhesive component/components at another site. Since the semi-finished product according to the invention is intended to be produced at a small number of high-tech central production sites and then dispatched to the users, e.g. hospitals at home and abroad, storage periods of several months may pass before the workpieces can be surgically implanted. Throughout this period, which can easily span six to twelve months, the sterility of the workpiece must be guaranteed.

Upon use, the protective layer, which is not an end layer but instead an adhesive component of a multi-component adhesive, can be coated in situ with a second adhesive component, e.g. a sterile MMA monomer, and thereby activated. Directly thereafter, these two components are then brought into contact with a third adhesive component, a polymeric adhesive.

Also according to the invention, the sterile and/or sterilizable preserving protective layer can be made of polymethyl methacrylate. Such a protective layer is particularly expedient in medicine if the workpiece is to be fitted as an implant in a bone.

Also according to the invention, the sterile and/or sterilizable preserving protective layer can be made of BisGMA. A protective layer made of BisGMA is particularly intended for use in dentistry.

Also according to the invention, the preserving protective layer can be made of epoxy resin. A protective layer made of epoxy resin is particularly intended for use in the technical non-biological sector.

Also according to the invention, the preserving protective layer can be made of phenolic resin. A protective layer made of phenolic resin is particularly intended for use in the technical non-biological sector.

Also according to the invention, the sterile and/or sterilizable preserving protective layer can have a thickness of <100 $\mu$m. A thin protective layer such as this can be activated very quickly by wetting with a corresponding monomer. This layer is also chosen to be sufficiently thick to provide protection against abrasion during transportation.

Also according to the invention, the substrate can have a surface conditioned to form a stable connection to a polymeric adhesive.

Also according to the invention, the workpiece can be used in moist warm media.

Also according to the invention, the workpiece can be used as an implant or prosthesis or as a component of an implant or prosthesis in medicine. This relates in particular to implants in the form of sterile and/or sterilizable, coated hip endoprosthesis shafts, knee-joint prosthesis shafts and other joint prosthesis shafts.

The invention also relates to a method for producing a workpiece of the above type, in which the surface of the substrate is cleaned, a silica layer is then applied using a high-vacuum evaporation unit and is then wetted with a silane coupling agent. After the substrate surface has been cleaned, carboxyl groups can be generated thereon by means of a low-pressure plasma process. In order to preserve the surface which has been treated in this way, with the silica layer and the silane coupling agent, until further processing, a sterile and/or sterilizable preserving protective layer is applied as the activatable first component of a multi-component adhesive which at the time of use is formed by addition of at least one further adhesive component. The substrate surface, which has usually already been pre-cleaned, thus undergoes further cleaning by means of the low-pressure plasma process. By selection of a suitable plasma gas, carboxyl groups can be generated on the cleaned substrate surface for activation, which greatly increases the adhesive bonding strength. By applying a sterile and/or sterilizable preserving protective layer, workpieces are produced which can be stored and transported.

Also according to the invention, the vapour-deposition of the silica layer can be effected in a reproducible manner using a shutter system. It is additionally possible to provide a tri-axial unit with which a silica layer of constant thickness can be realized on a complex 3D surface.

The invention also relates to a method for making use of a workpiece of the above type, where the workpiece, after sterile intermediate storage, is first provided on its conditioned surface with a monomeric adhesive component in order to activate the protective layer and a polymeric adhesive component is then applied on top of this, these two adhesive components forming a multi-component adhesive together with the protective layer. By means of the activation of the preserving protective layer with the monomeric adhesive component, the protective layer can chemically react with the polymeric adhesive component layer which is to be applied. By storing the workpiece under sterile conditions, for example under He or $N_2$ protective gas in a gastight blister pack, it can be stored for a number of months until further processing.

The workpiece according to the invention and the methods for producing and for making use of said workpiece are explained below with reference to a hip endoprosthesis shaft.

A low-pressure plasma process is used to generate carboxyl groups on a cleaned metallic shaft of a hip endoprosthesis, which carboxyl group increase the adhesive bonding strength of a silica layer which is to be vapour-deposited onto it. This silica layer is preferably wetted in a monomolecular manner with a silane coupling agent, and a sterile and/or sterilizable preserving protective layer is then applied thereon.

The hip endoprosthesis which has been produced in this way consequently has a metallic shaft with a silica layer, on top of this a layer of silane coupling agent, and a final sterile and/or sterilized preserving layer (first adhesive component).

After production, the hip endoprosthesis according to the invention is packed in a sterile manner, for example in a gastight blister pack filled with He or $N_2$ protective gas. In this way it is protected from contamination and can be transported and also stored for a number of months without any loss of quality. The coated shaft of the hip endoprosthesis is then removed from the sterile pack in site under sterile conditions in the operating theatre and coated with a sterile MMA monomer (further adhesive component). The sterile preserving protective layer is activated in this way. Directly thereafter, the shaft is inserted into a bone cavity filled with the polymeric adhesive (bone cement=further adhesive component). After the adhesive sets, a connection between the adhesive and the hip endoprosthesis shaft is obtained which has a high degree of adhesive bonding and is stable for a long period of time in the moist and warm conditions within the body.

What is claimed is:

1. Workpiece with a substrate of ceramic, metal or polymer, the substrate having a surface which is conditioned to form a stable connection with a polymer and which is provided with a silica layer and, on top of this, with a silane coupling agent, characterized in that the substrate, the silica layer and the silane coupling agent are sterile, and on top of the silane coupling agent, there is a preserving protective layer which is a polymethyl methacrylate, a Bis GMA, an epoxy resin or a phenolic resin and is sterile and/or can be sterilized after polymerization, said protective layer being an activatable first component of a multi-component adhesive which can be formed at the time of use by addition of at least one further adhesive component.

2. Workpiece according to claim 1, characterized in that the sterile and/or sterilizable preserving protective layer is made of polymethyl methacrylate.

3. Workpiece according to claim 1, characterized in that the sterile and/or sterilizable preserving protective layer is made of BisGMA.

4. Workpiece according to claim 1, characterized in that the sterile and/or sterilizable preserving protective layer is made of epoxy resin.

5. Workpiece according to claim 1, characterized in that the sterile and/or sterilizable preserving protective layer is made of phenolic resin.

6. Workpiece according to claim 1 characterized in that the sterile and/or sterilizable preserving protective layer has a thickness of <100 μm.

7. Workpiece according to claim 1 characterized in that the substrate has a surface conditioned to form a stable connection to said protective layer.

8. Method for producing a workpiece as claimed in claim 1 which comprises cleaning the surface of a substrate, applying a silica layer to the cleaned substrate using high-vacuum evaporation and wetting the silica layer on the substrate with a silane coupling agent, characterized by the steps of generating carboxyl groups thereon by means of a low-pressure plasma process after the substrate surface has been cleaned, and applying to the cleaned surface on which carboxyl groups have been generated a sterile and/or sterilizable preserving protective layer which is a polymethyl methacrylate, a Bis GMA, an epoxy resin or a phenolic resin and is the activatable first component of a multi-component adhesive which can be formed at the time of use by addition of at least one further adhesive component.

9. Method for producing a workpiece according to claim 8, characterized in that the vapour-deposition of the silica layer is effected in a reproducible manner using a shutter system.

10. Method for using a workpiece as claimed in claim 1, characterized in that after sterile intermediate storage, the workpiece is first provided on its conditioned surface with a monomeric adhesive component in order to activate the protective layer, and a polymeric adhesive component is then applied on top of the activated protective layer, the monomeric and polymeric adhesive components forming, with the protective layer, a multi-component adhesive.

* * * * *